(12) United States Patent
Piper

(10) Patent No.: US 12,053,648 B2
(45) Date of Patent: Aug. 6, 2024

(54) FOCAL THERAPY PRE-PLANNING AND PREDICTIVE FUSION

(71) Applicant: MIM SOFTWARE INC., Cleveland, OH (US)

(72) Inventor: Jonathan William Piper, Orange, OH (US)

(73) Assignee: MIM SOFTWARE INC., Cleveland, OH (US)

( * ) Notice: Subject to any disclaimer, the term of this patent is extended or adjusted under 35 U.S.C. 154(b) by 278 days.

(21) Appl. No.: 17/062,224

(22) Filed: Oct. 2, 2020

(65) Prior Publication Data

US 2022/0001207 A1 Jan. 6, 2022

Related U.S. Application Data

(60) Provisional application No. 63/047,318, filed on Jul. 2, 2020.

(51) Int. Cl.
| | | |
|---|---|---|
| *A61N 5/10* | (2006.01) | |
| *G06T 7/00* | (2017.01) | |
| *G16H 20/40* | (2018.01) | |
| *G16H 30/40* | (2018.01) | |

(52) U.S. Cl.
CPC .......... *A61N 5/1039* (2013.01); *G06T 7/0012* (2013.01); *G16H 20/40* (2018.01); *G16H 30/40* (2018.01)

(58) Field of Classification Search
CPC .......... G16H 20/40; G16H 30/40; A61N 7/02; A61N 5/1039; A61B 34/10; G06T 7/0012; G06T 5/50; A61F 7/00
See application file for complete search history.

(56) References Cited

U.S. PATENT DOCUMENTS

| | | |
|---|---|---|
| 2007/0129633 A1 | 6/2007 | Warren et al. |
| 2009/0054772 A1 | 2/2009 | Lin et al. |
| 2015/0169836 A1 | 6/2015 | Vahala et al. |
| 2016/0279444 A1 | 9/2016 | Schlosser |
| 2018/0147419 A1 | 5/2018 | Heese et al. |
| 2020/0155870 A1* | 5/2020 | Takahashi ............ A61N 5/1067 |

OTHER PUBLICATIONS

Intl. Search Report and Written Opinion of the Intl. Searching Authority; PCT/US2021/040232; Dec. 20, 2021; 18 pgs.

* cited by examiner

*Primary Examiner* — Mark D Remaly
(74) *Attorney, Agent, or Firm* — TUCKER ELLIS LLP; Evan T. Perry

(57) ABSTRACT

A planning and fusion system provides enhanced planning of focal therapy. Treatment zones are virtually planned on MR image data. The treatment plan generated on MR image data is registered to a second modality associated with a treatment device.

20 Claims, 12 Drawing Sheets

FOCAL THERAPY PRE-PLANNING AND PREDICTIVE FUSION

CROSS-REFERENCE TO RELATED APPLICATIONS

This application is a non-provisional of and claims priority to U.S. Provisional Patent Application Ser. No. 63/047,318, filed on Jul. 2, 2020. This application is also related to U.S. patent application Ser. No. 15/425,748, filed on Feb. 6, 2017 and entitled "SYSTEM AND METHOD OF APPLYING AN ARBITRARY ANGLE TO REFORMAT MEDICAL IMAGES", and U.S. patent application Ser. No. 15/970,973 (now U.S. Pat. No. 10,621,737), filed on May 4, 2018 and entitled "SYSTEM AND METHOD FOR PREDICTIVE FUSION". The entireties of the aforementioned applications are herein incorporated by reference.

TECHNICAL FIELD

This application relates generally to focal therapy planning and, more particularly, to systems and methods for pre-planning therapy with predictive fusion to a treatment domain.

BACKGROUND OF THE INVENTION

Image fusion generally relates to combining information from different images into a single, composite image. In medical imaging, for instance, fusion can involve registering and combining different images, in some manner, to generate a composite image. The composite image can provide improved image quality or enhance usability of the images for diagnosis, treatment planning and assessment, tracking disease progression, etc. In medical imaging, the two or more images fused can be of the same imaging modality or different imaging modalities. Multiple images of the same modality may be fused to ascertain disease progression or treatment efficacy. Images of different modalities can be combined to leverage benefits of the differing modalities for planning purposes or for convenience.

For instance, magnetic resonance imaging (MRI) provides good soft tissue contrast. Thus, MRI enables relatively easy differentiation of lesions or other abnormalities from healthy tissue. Accordingly, MRI performs well for detection and planning. MRI, however, can be inconvenient for intra-operative guidance due to cost and non-portability of the imaging machine. For example, some procedures (e.g., taking a biopsies of a prostate) may often guided by ultrasound, which is portable and provides high spatial resolution. Compared to MRI, however, ultrasound provides less tissue discrimination. An MRI-ultrasound fusion can combine information from the respective modalities to improve execution of the procedure.

BRIEF SUMMARY OF THE INVENTION

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of the summary is to present some concepts related to some exemplary non-limiting embodiments in a simplified form as a prelude to the more detailed description of the various embodiments that follow.

In various, non-limiting embodiments, a system and associated methods are provided for improved planning of focal therapy. According to an aspect, treatment zones are virtually planned on MR image data. The treatment plan generated on MR image data may include predictive fusion information. According to an example, the predictive fusion information may include portions of the treatment plan transformed in accordance with an expected or desired position of a treatment device and/or an intra-procedural imaging device. In other words, the predictive fusion information predicts the fusion of the MR image data and/or portions of the treatment plan with yet to be acquired image data of a different modality. Furthermore, the predictive fusion information guides the operator to position the treatment or imaging device in order to align the treatment target with the treatment plan.

These and other embodiments are described in more detail below.

BRIEF DESCRIPTION OF THE DRAWING

Various non-limiting embodiments are further described with reference the accompanying drawings in which.

DETAILED DESCRIPTION OF THE INVENTION

Figure 1:
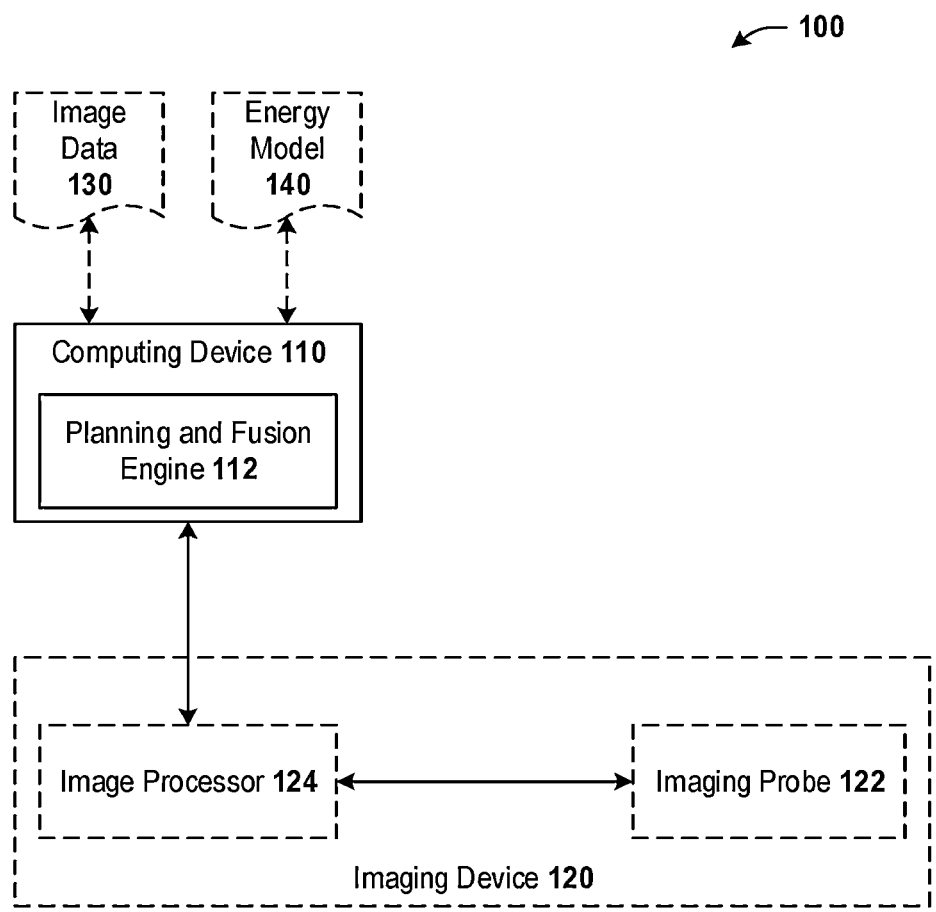
FIG. 1 is a block diagram of an exemplary, non-limiting embodiment for a planning and fusion system according to one or more aspects.

As discussed in the background, medical image fusion can leverage strengths of different imaging modalities and generate combined information having a wide array of applications. For instance, a fusion of MRI and ultrasound images can provide intra-procedural imaging with accurate identification of anatomical features. In one example, focal therapy (e.g. cryotherapy or high-intensity focused ultrasound (HIFU) of a lesion of a prostate can benefit from image fusion. A typical workflow may involve an imaging step with, for example, an ultrasound probe aimed at a lesion. From the imaging, treatment zones are planned and high resolution scan is performed. The scan data may be fused with other imaging (e.g. MRI) in fusion software. With the fused image data, a lesion and/or other anatomical features (e.g. prostate, urethra, etc.) may be contoured using the US and/or MR image data. The contour information can be sent to a treatment device, which in the case of HIFU treatment, may be a device that delivers focused ultrasound energy to ablate target tissue. After transfer of contour information, additional modifications may be needed to finalize the treatment plan.

In various, non-limiting embodiments, a system and associated methods are provided for improved planning of focal therapy. According to an aspect, treatment zones are virtually planned on MR image data based on energy models that describe the zones which may be ablated lethally by the treatment device. The treatment plan generated on MR image data may include predictive fusion information. According to an example, the predictive fusion information may include portions of the treatment plan transformed in accordance with an expected or desired position of a treatment device and/or an intra-procedural imaging device. In other words, the predictive fusion information predicts the fusion of the MR image data and/or portions of the treatment plan with yet to be acquired image data of a different modality.

For instance, the treatment plan may include feature information associated with previously acquired image data (e.g. MR image data). The feature information may include positions and orientations of anatomical features, contours of anatomical features, contours of targets (e.g. lesions), expanded target contours (e.g. margins), treatment positions, treatment fields-of-view, treatment zones, and the like. The feature information can be transformed so as to indicate the associated features from the perspective of the treatment or intra-procedural imaging device. The predictive fusion information enables proper alignment of the treatment device and/or intra-procedural imaging device prior to applying the treatment in accordance with the treatment plan. The intra-operative fusion may be performed with software overlays or images or contours or may be performed cognitively where the operator aligns the treatment or imaging device based on visual side-by-side assessment of concordance with the treatment plan.

In one embodiment, a system is provided that includes a processor coupled to memory storing computer-executable instructions. When executed by the processor, the instructions configure the processor to: obtain feature information indicative of one or more features in an image of a first modality; combine the image with a phantom image or virtual treatment indication that indicates a field of view and/or one or more treatment zones of a treatment device; determine a zone-specific target area for each of one or more treatment zones associated with a treatment device; and register the image along with at least one of the zone-specific target areas or the feature information to a second modality associated with the treatment device. In an example, the processor is further configured to reslice the image based on a predetermined orientation of the treatment device and update the feature information according to the resliced image. The resliced image is combined with the phantom image or virtual treatment indication.

As mentioned above, in various embodiments, a procedure can be virtually planned in a first modality and predictive fusion information can be generated to facilitate utilization of the treatment plan with a treatment device and/or intra-procedural imaging device of a second modality.

FIG. 1 shows a block diagram illustrating an exemplary, non-limiting embodiment for a planning and fusion system 100. As shown, system 100 can include a computing device 110 and an imaging device 120. The computing device 110 can include a processor and various computer-readable storage media (e.g., volatile and non-volatile). The computer-readable storage media can store computer-executable instructions implementing at least a portion of functional modules comprising a planning and fusion engine 112, described herein. When the computer-executable instructions are executed by the processor, the system 100 is thus configured to perform the operations described herein.

Computing device 110 can further include various hardware devices (not shown) to implement portions of planning and fusion engine 112. For instance, computing device 110 can include a graphics device having a graphics processing unit (GPU), dedicated memory, and/or hardware interfaces to couple the graphics device to a display. Moreover, computing device 110 can include physical hardware ports and/or wireless interfaces (e.g., Bluetooth, wireless USB, etc.) to couple computing device 110 to various devices of system 100, such as, but not limited to imaging device 120.

Imaging device 120, as shown, can include an imaging probe 122 and an image processor 124. In an aspect, imaging device 120 can be a portable device suitable for intra-procedural imaging, such as an ultrasound imaging device. In another aspect, imaging device 120 may also be a treatment device. For instance, imaging device 120 may be an HIFU device capable of delivering ultrasound energy to ablate target tissue. Accordingly, in some aspects, imaging device 120 may also be a treatment device. Nonetheless, it is to be appreciated that features and aspects described and claimed herein are not limited to ultrasound applications and can be readily adapted for use with other imaging modalities. In the ultrasound example, imaging probe 122 can include one or more transducer arrays configures to emit ultrasonic pulses and receive echoes. The echoes can be converted to electrical signals and provided to image processor 124 to generate an ultrasound image.

Planning and fusion engine 112, according to an aspect, enables planning of a treatment to be performed with and/or facilitated by imaging device 120. Planning and fusion engine 112 utilizes image data 130, which can include previously acquired image data of a different modality, for example, and optionally an energy model 140 (e.g. which describes ablation zones of a treatment device) to generate a treatment plan and/or predictive fusion information that can be communicated to imaging device 120 for execution. To illustrate, consider a focal therapy of a lesion of a prostate. Image data 130 can include imaging of the prostate in a different modality from that produced by the imaging device 120. The modality of image data 130 may provide better tissue discrimination capabilities so that the prostate can be readily identified and healthy tissue of the prostate can be differentiated from abnormal tissue. Using image data 130, a plan for focal therapy can be defined. Planning and fusion engine 112 can predictively fuse at least a portion of the treatment plan to yet to be acquired image data from imaging device 120. Such predictive fusion information facilitates alignment of image device 120 and/or treatment device prior to treatment.

Figure 2:
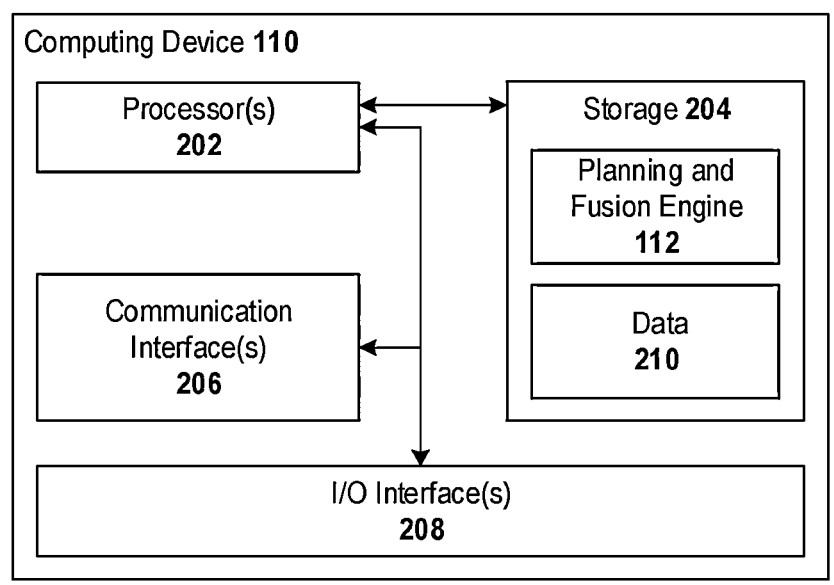
FIG. 2 is a schematic block diagram of an exemplary, non-limiting embodiment for a computing device associated with the planning and fusion system of FIG. 1.

FIG. 2 illustrates a schematic block diagram of an exemplary, non-limiting embodiment for a computing device 110 associated with system 100 of FIG. 1. As shown in FIG. 2, computing device 110 includes one or more processor(s) 202 configured to executed computer-executable instructions such as instructions composing planning and fusion engine 112. Such computer-executable instructions can be stored on one or more computer-readable media including non-transitory, computer-readable storage media such as storage 204. For instance, storage 204 can include non-volatile storage to persistently store planning and fusion engine 112 and/or data 210 (e.g., image data, feature information, phantom information, treatment device information, configuration information, treatment plan information, working data, etc.). Storage 204 can also include volatile storage that stores planning and fusion engine 112 and other data 210 (or portions thereof) during execution by processor 202.

Computing device 110 includes a communication interface 206 to couple computing device 110 to various remote systems (e.g. an image data store, an imaging apparatus, etc.). Communication interface 206 can be a wired or wireless interface including, but not limited, a WiFi interface, an Ethernet interface, a fiber optic interface, a cellular radio interface, a satellite interface, etc. An I/O interface 208 is also provided to couple computing device 110 to various input and output devices such as displays, touch screens, keyboards, mice, touchpads, etc. By way of example, I/O interface 208 can include wired or wireless interfaces such as, but not limited to, a USB interface, a serial interface, a WiFi interface, a short-range RF interface (Bluetooth), an infrared interface, a near-field communication (NFC) interface, etc.

Figure 3:
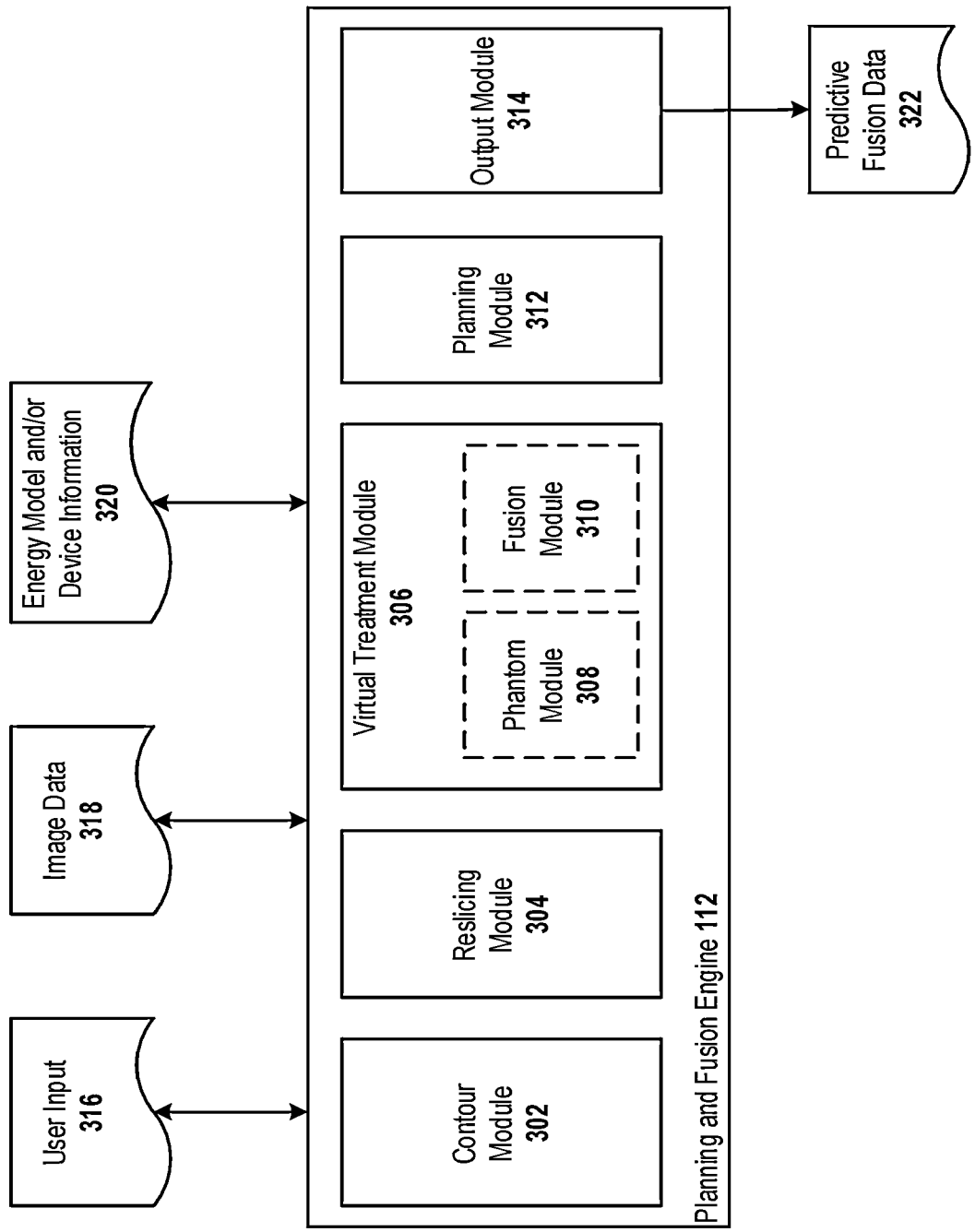
FIG. 3 is a schematic block diagram of an exemplary, non-limiting embodiment for planning and fusion according to one or more aspects.

Turning now to FIG. 3, a block diagram of an exemplary, non-limiting planning and fusion engine 112 is depicted. As shown in FIG. 3, planning and fusion engine 112 can include various functional modules implemented by computer-executable instructions. The modules can include a contour module 302, a reslicing module 304, a virtual treatment module 306, a planning module 312, and an output module 314.

Contour module 302 include automatic and/or manual tools for contouring features of images. For example, contour module 302 can receive user input 316 and image data 318 and generate feature information. In general, the term "feature information" relates to imaging or other data that specifies a pose of a feature or object in images. As utilized herein, the term "pose" refers to a position and orientation of an object in a given frame of reference, which can be defined relative to another object. By way of example, the pose of a feature in an image relates to the position and orientation of the feature as shown in the image or within the imaging space or volume. In an example related to focal therapy of a prostate, feature information may include a contour of the prostate and a separate contour for the abnormal tissue. In addition to specifically delineating features in image data 318, contour module 302 may also apply customizable margins to one or more features. For example, a margin may be applied around abnormal tissue to decrease a likelihood that portions of the tissue are not treated. As utilized herein, the terms "target" or "treatment target" refer to, for example, the abnormal tissue for which a treatment is planned as described herein.

Reslicing module 304 reslices or resamples image data 318 according to an input reference orientation. For example, image data 318 may include voxel data corresponding to a three-dimensional volume. Reslicing may involve slicing the image data 318 along a virtual imaging plane, which may include interpolating image data corresponding to the virtual imaging plane. In an example, the virtual imaging plane may be defined based on an orientation of a probe of a treatment device.

Reslicing, in some examples, may involve multiple angles. For instance, the virtual imaging plane above may be oriented at a first angle with respect to the imaging volume. A second or more angles may also be utilized during reslicing. Accordingly, a three-dimensional rotation or, generally, multiple rotations may be performed to transform image data 316 with respect to a desired orientation(s).

In yet another example, reslicing may be performed relative to the target as opposed to another anatomical feature. In this embodiment, a treatment zone may better conform to the target.

Virtual treatment module 306 provides a virtual treatment template in association with image data 318 (which may be resliced image data generated by reslicing module 304) with which a treatment plan can be created. The virtual treatment template may be defined, in part, based on energy model and/or device information 320. The energy model defines ablation zones for a HIFU treatment device, for example. The device information 320 may additionally provide field of view information of a treatment device. Based on this information, the virtual treatment template may be created and displayed on image data 318, which may be resliced as described above.

In one embodiment, a phantom module 308 provides a phantom image data based on, for example, phantom information. The phantom image data may include virtual image data in a modality of a treatment device (and/or an intra-procedural imaging device). The phantom information may indicate characteristics of the treatment device so that the phantom module 308 can include a field of view and/or transmit zones (e.g. ablation zones) in the phantom image data.

Fusion module 310 is configured to fuse image data. The image data fused, in some examples, may correspond to different modalities. For example, fusion module 310 may fuse resliced image data generated by reslicer module 304 with phantom image data generated by phantom module 308. In the case of an ultrasound treatment device and MR image data, the fused image data may include feature information created with contour module 302 and MR image data together with an overlay indicative of a field of view and transmit zones of the treatment device. After fusion, the virtual treatment template is provided on image data 318. It is to be appreciated that fusion with a phantom image is one embodiment to generating the virtual treatment template. The template, in other embodiments, can be directly generated and overlaid on the image data 318 using more general information, such as the energy model and device information 320.

Utilizing the virtual treatment template, a treatment plan can be further developed. For example, planning module 312 includes manual or automatic tools to position, truncate, or otherwise edit ablation zones based on feature information (e.g. prostate contours, lesion contours, margins, etc.). For example, the zones may be positioned, including overlapping of zones, in an optimal manner. The optimization may be automatic or semi-automatic. Further, the optimization may be a forward optimization or an inverse planning. Inverse planning may involve, for example, imaging with a treatment device, positioning the probe, registering, and then planning treatment zones.

The treatment plan (e.g. image data, contours, positioned and edited zones, etc.) can be transformed by output module 314 to generate predictive fusion data 320. According to one aspect, predictive fusion data 320 may include portions of the treatment plan registered to a three-dimensional imaging volume (e.g. a volume corresponding to the treatment device). Thus, the predictive fusion data 320 aligns the feature contours, planned zones, etc. to a predicted or expected orientation with respect to the treatment device. The predictive fusion data 320 facilitates verifying a position of the treatment device prior to executing treatment in accordance with the plan. For instance, the predictive fusion data 322 guides an operator to position the treatment or imaging device in order to align the treatment target with the treatment plan. This intra-operative fusion may be performed with software overlays or images or contours or may be performed cognitively where the operator aligns the treatment or imaging device based on visual side-by-side assessment of concordance with the treatment plan.

Figure 4:
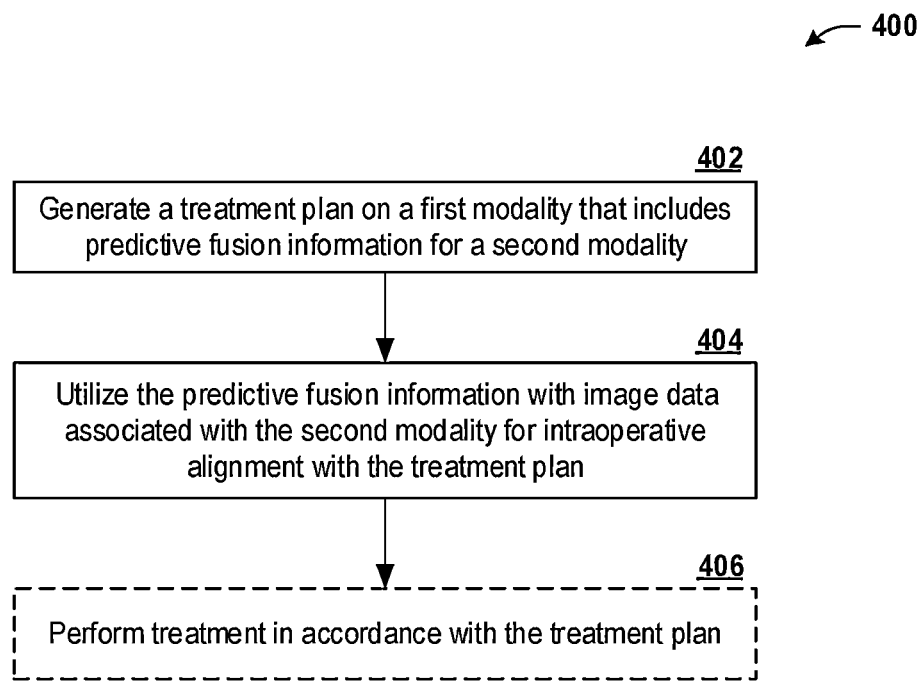
FIG. 4 is a flow diagram of an exemplary, non-limiting method for planning and performing a procedure in accordance with various aspects.

FIG. 4 illustrates a flow diagram of an exemplary, non-limiting method 400 for planning and performing a procedure. The method 400 can be performed, for example, by system 100 and/or planning and fusion engine 112 executed on computing device 110 as described previously. Method 400 may begin at 402, wherein a treatment plan is generated on a first modality. The treatment plan includes predictive fusion information for a second modality. For example, the first modality may be MR and the second modality may be ultrasound.

At 404, the predictive fusion information is utilized with image data associated with the second modality for intra-operative alignment of a treatment device with the treatment plan. At 406, the procedure may be performed with the treatment device.

Figure 5:
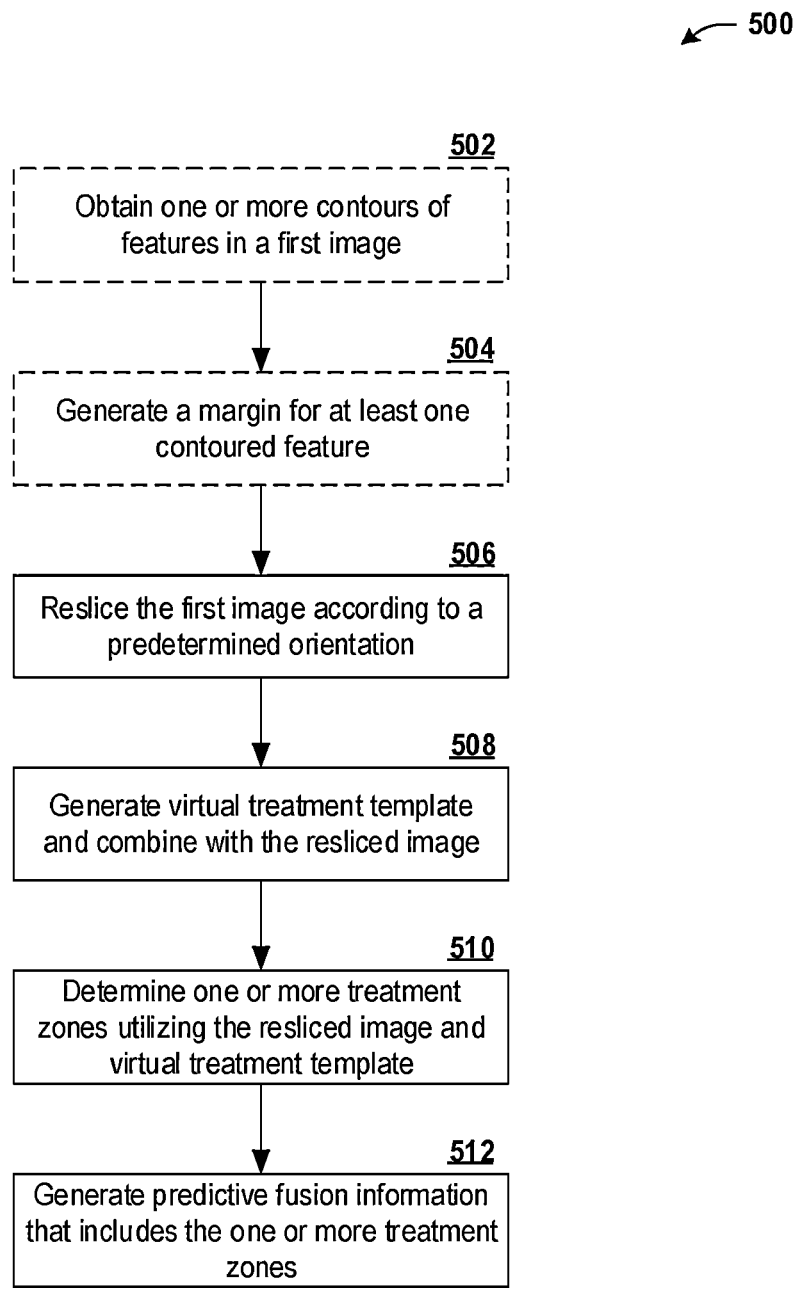
FIG. 5 is a flow diagram of an exemplary, non-limiting method for planning a procedure and predicting a fusion between at least two image modalities in accordance with the planned procedure.

Turning to FIG. 5, illustrated is a method 500 for a planning a procedure and predicting a fusion between at least two image modalities in accordance with the planned procedure. Method 500 can be performed, for example, by system 100 and/or planning and fusion engine 112 executed on computing device 110 as described previously. In one aspect, method 500 may correspond to step 402 of method 400.

Figure 6:
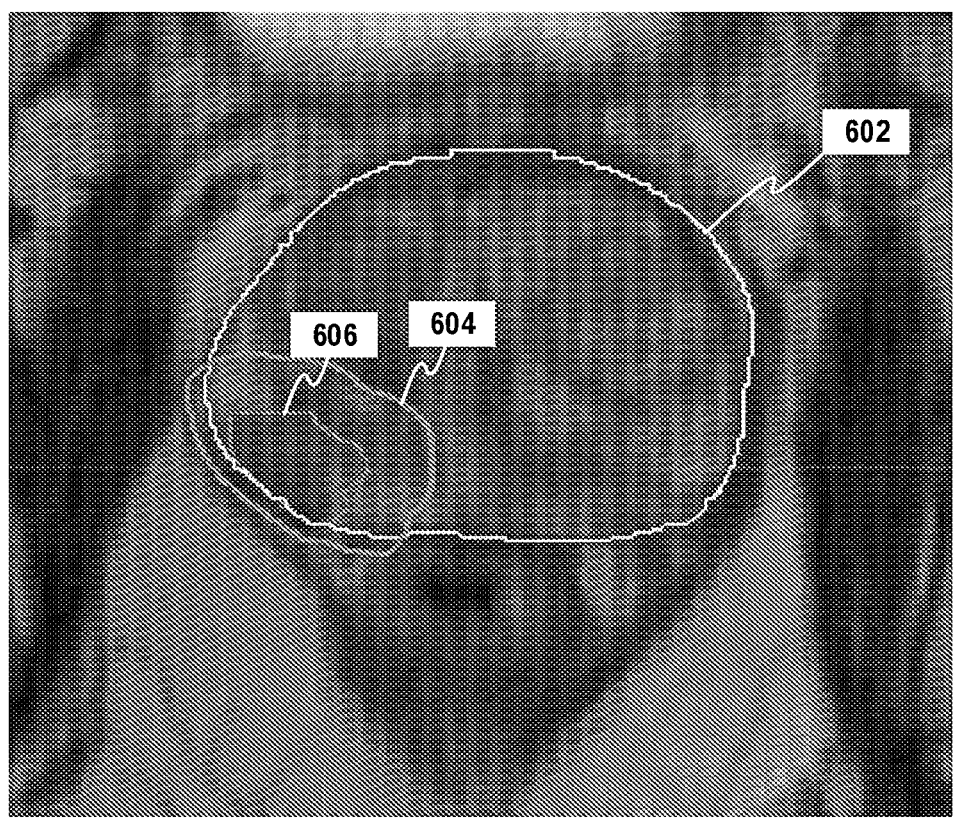
FIG. 6 is an exemplary image having contours overlaid to indicate various features of the image.

At 502, one or more contours of various features in a first image are obtained. For example, FIG. 6 depicts an exemplary image showing various contours such as a prostate contour 602 and a lesion contour 606. At 504, a margin is added to at least one contoured features. For example, in FIG. 6, a margin 604 is shown added to lesion contour 606. According to an aspect, steps 502 and 504 are optional steps. For example, contour information and/or margin information may be pre-generated and obtained together with the image data.

Figure 7:
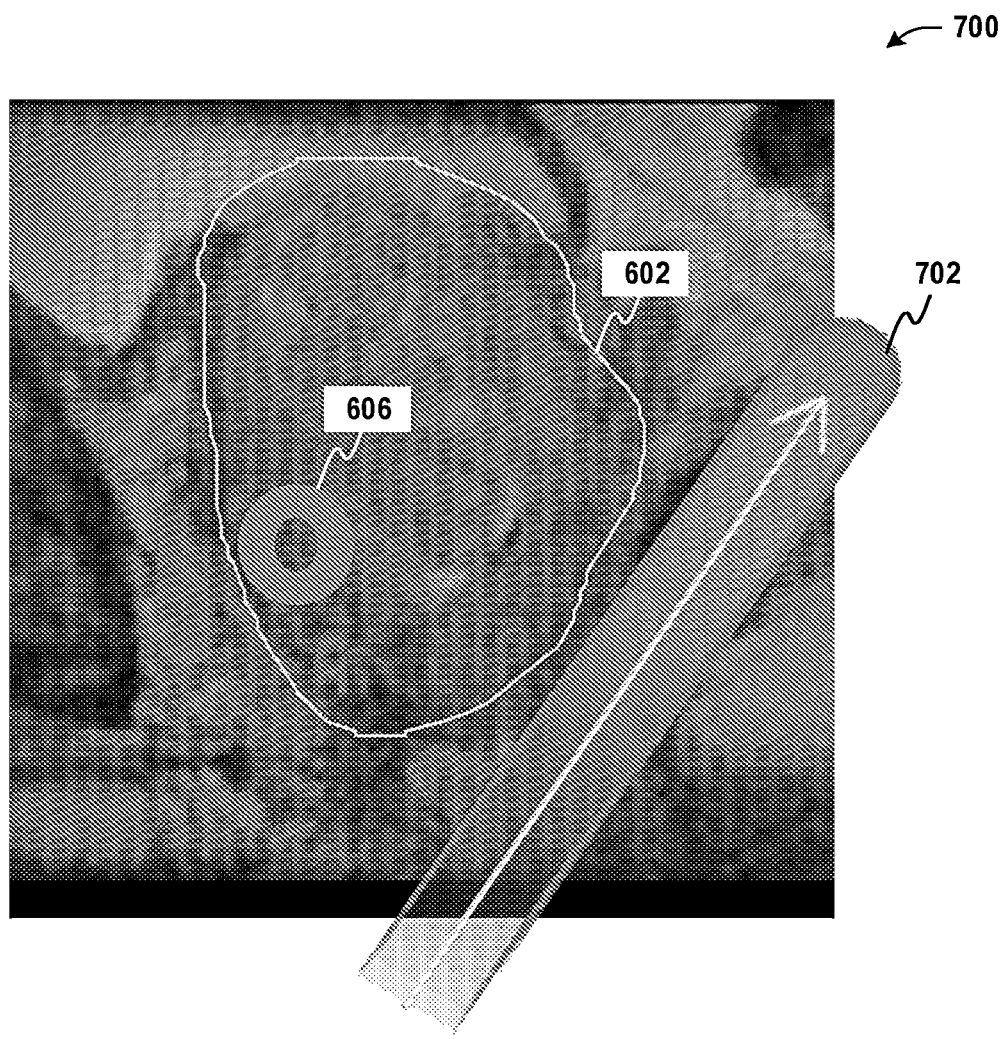
FIG. 7 is an exemplary image representing the image of FIG. 6 resliced based on an orientation corresponding to a procedure.

At 506, the first image (and contours) are resliced according to a predetermined orientation. In an example, as shown in FIG. 7, the orientation may correspond to a position of a treatment device. In FIG. 7, a resliced image showing the position of the treatment device 702, the prostate contour 602, and the lesion contour 606.

Figure 9:
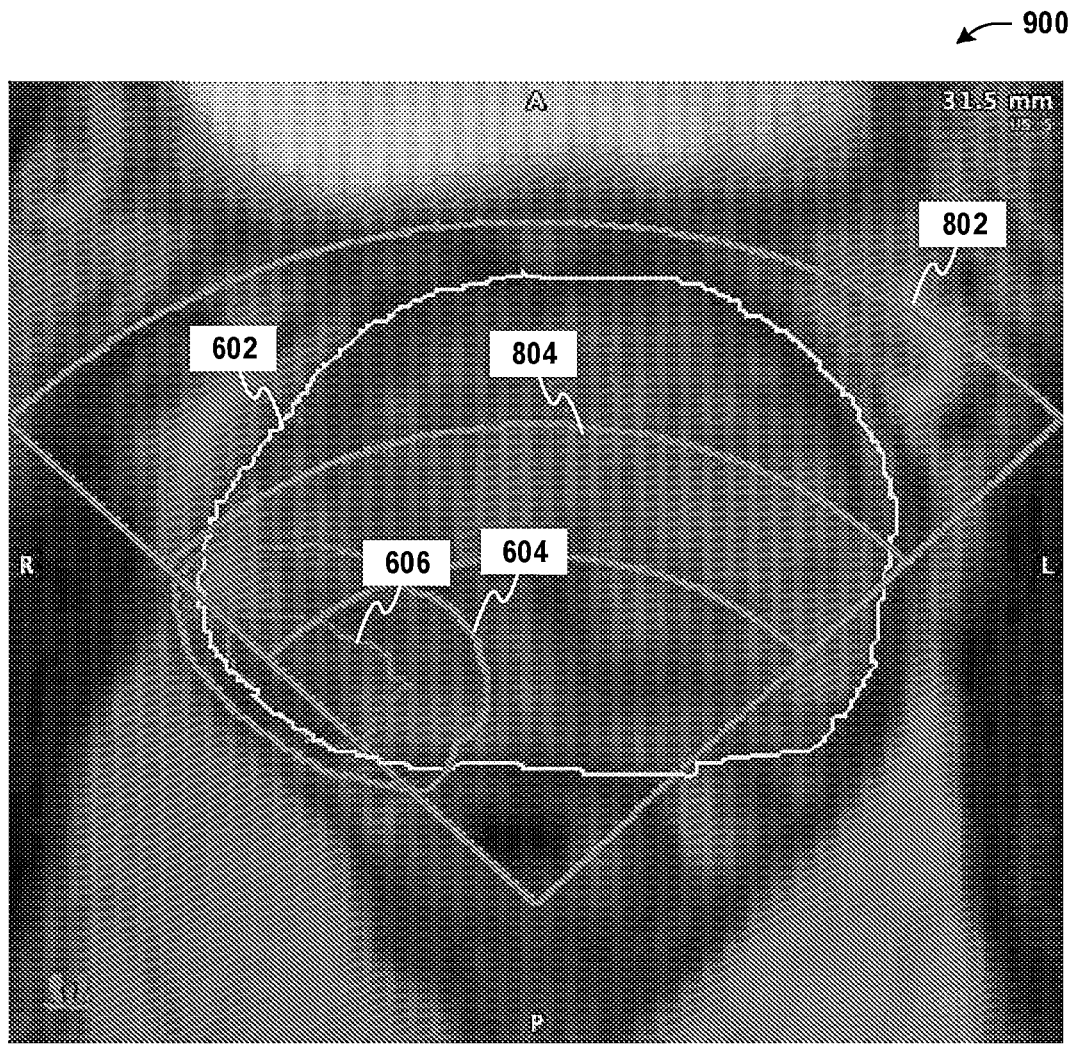
FIG. 9 is an exemplary image subsequent with a virtual treatment field.

At 508, a virtual treatment template is generated and combined with the resliced image from step 506. An exemplary image 900 depicting the virtual treatment template or virtual treatment field is shown in FIG. 9.

Figure 8:
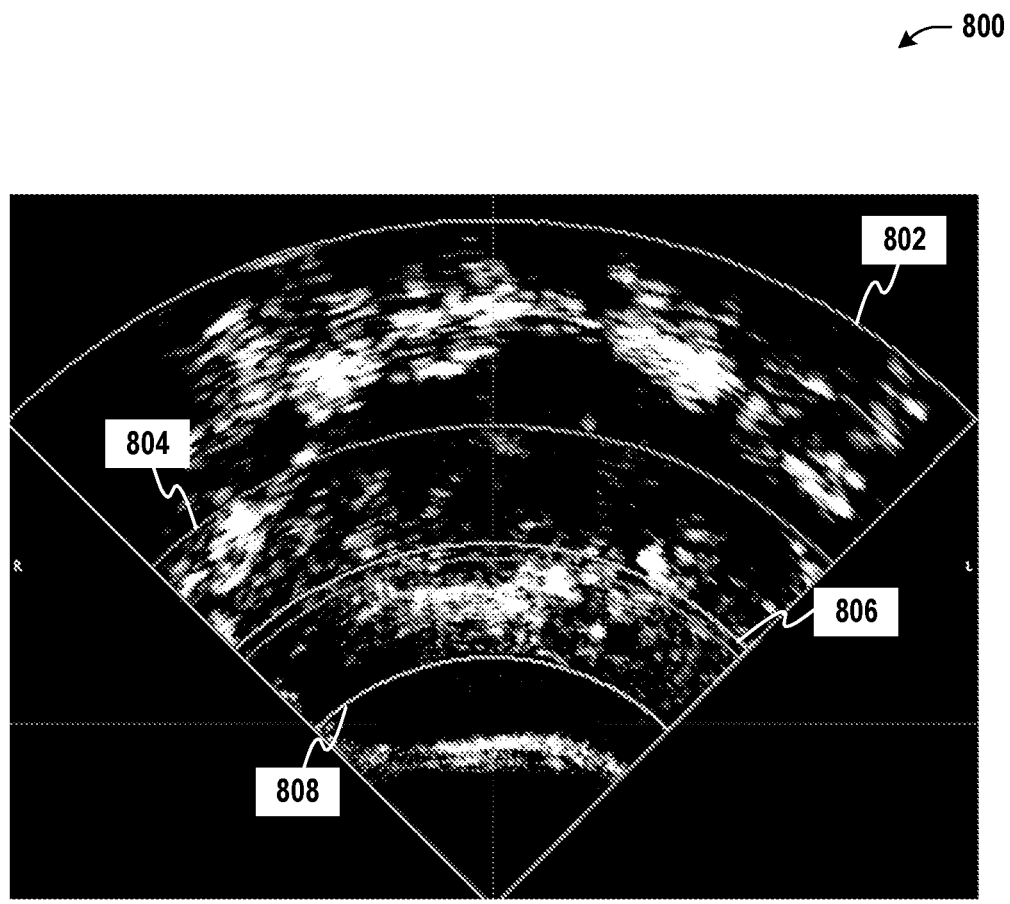
FIG. 8 is an exemplary phantom image with overlays indicating a field of view and treatment zone regions.

In an embodiment, the virtual treatment template may be generated based on phantom information and a phantom image. The phantom image is fused with the resliced image from step 506. An example phantom image 800 is depicted in FIG. 8 and includes a field of view 802, a first transmit zone 804, and a second transmit zone 808. According to an aspect, the transmit zones overlap as shown by the overlapping region 806. The overlap may be an optimized parameter.

Figure 10:
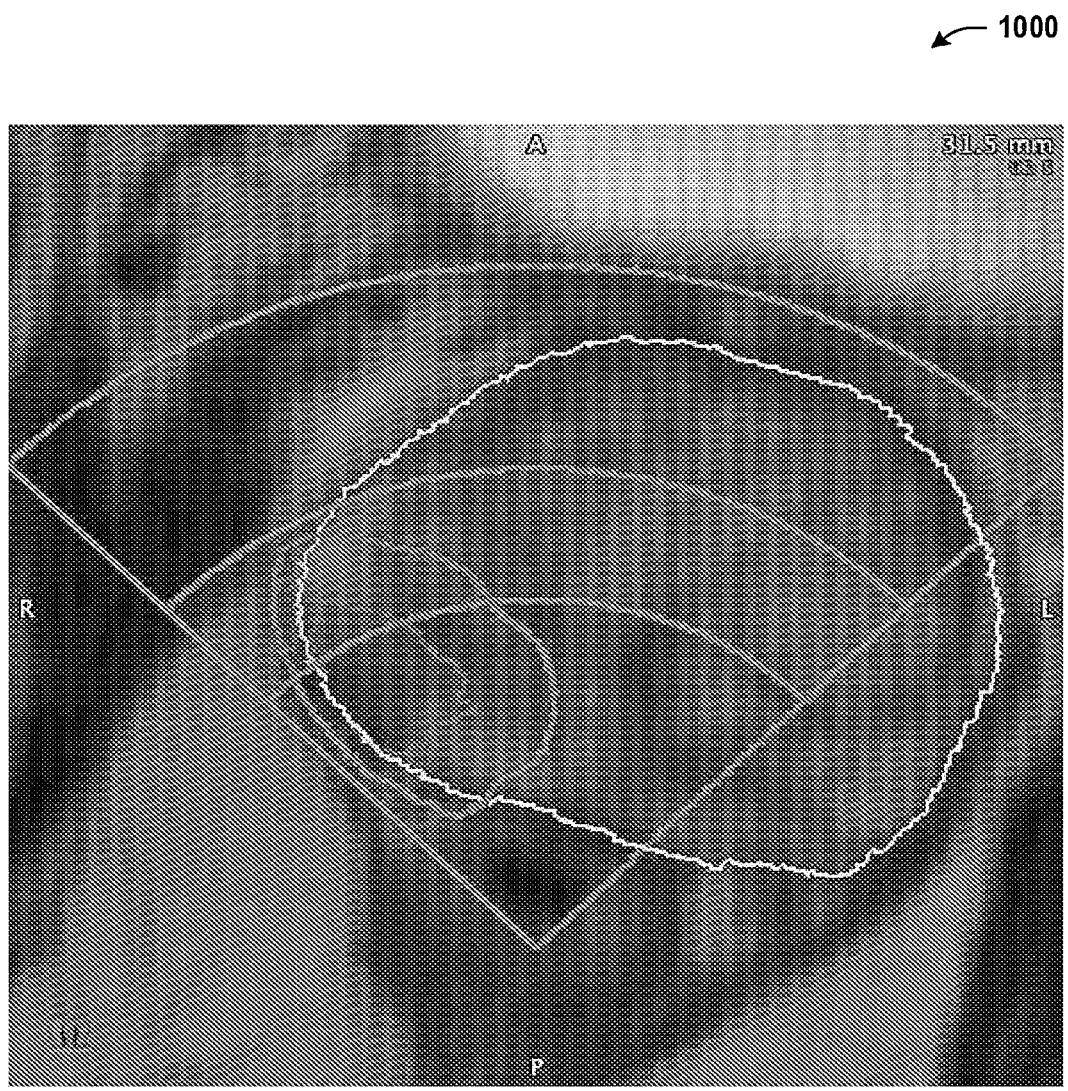
FIG. 10 is an exemplary image following a positioning of a target zone with respect to a target feature according to an aspect.
Figure 11:
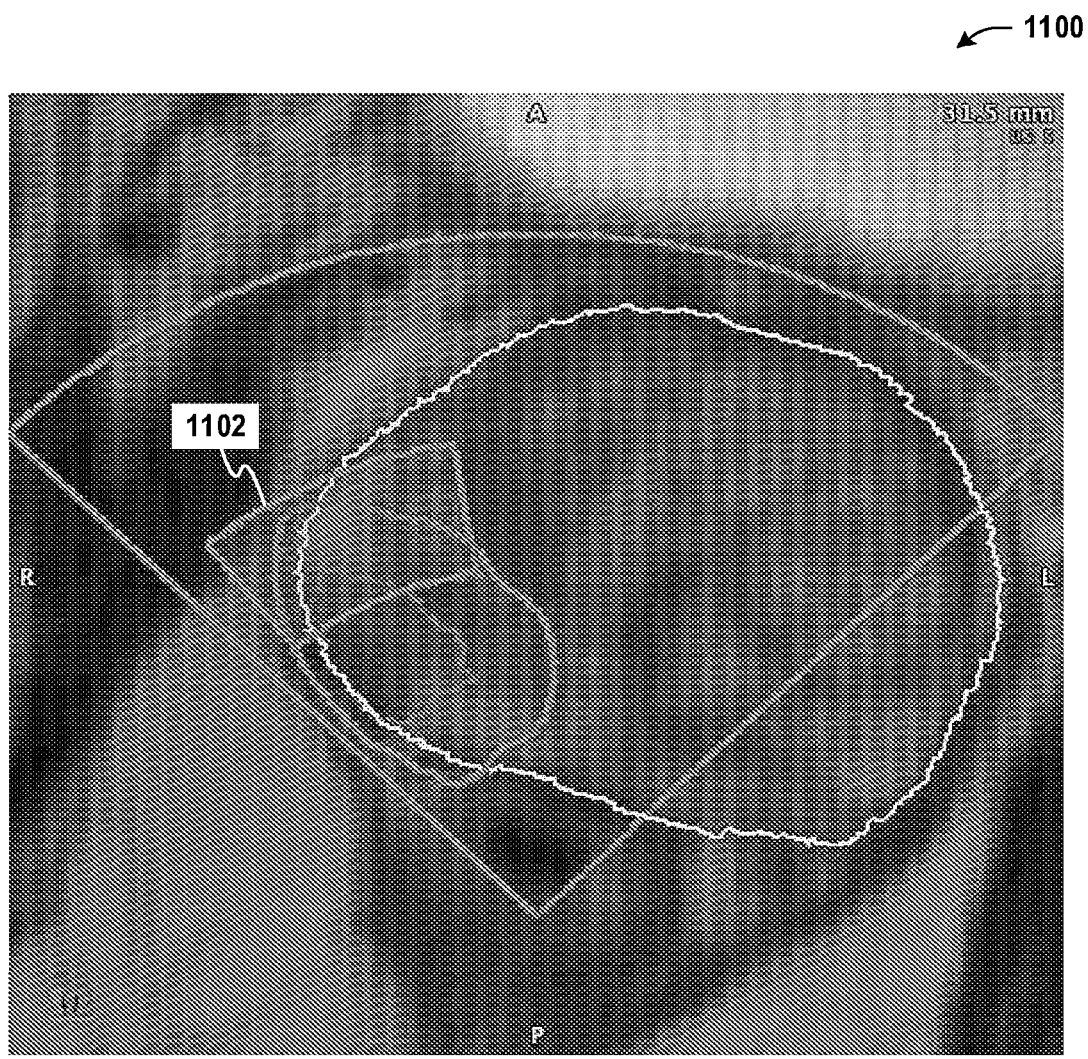
FIG. 11 is an exemplary image showing a zone-specific target area modified in accordance with the target feature.
Figure 12:
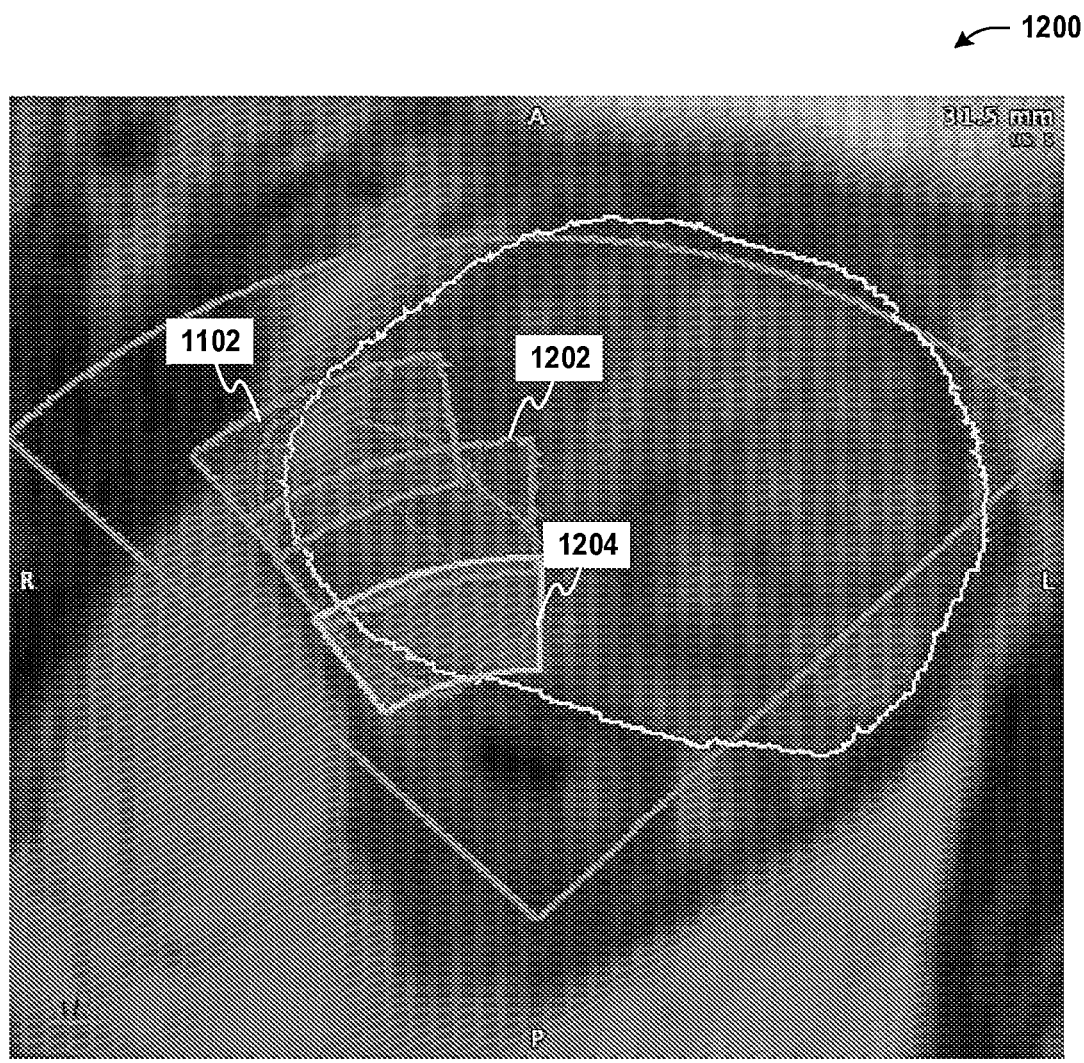
FIG. 12 is an exemplary image after planning additional zone-specific target areas for other zones.

At 510, one or more treatment zones utilizing the virtual treatment template are determined. For example, determining a treatment zone may include positioning the transmit or ablation zone by rotating as shown in FIG. 10. Then a zone specific treatment zone 1102 can be defined as shown in FIG. 11. The zone specific treatment zone may include portion of the transmit or ablation zone that intersects the lesion. This process is repeated for other transmit or ablation zones, which produces a one or more zone-specific treatment zones such as areas 1102, 1202, and 1204 as shown in FIG. 12.

At 512, predictive fusion information is generated that includes the one or more treatment zones. The predictive fusion information may include portions of the treatment plan (such as the one or more treatment zones, target contours, etc.) transformed in accordance with an expected or desired position of a treatment device and/or an intra-procedural imaging device. In other words, the predictive fusion information predicts the fusion of the MR image data and/or portions of the treatment plan with yet to be acquired image data of a different modality. Furthermore, the predictive fusion information guides the operator to position the treatment or imaging device in order to align the treatment target with the treatment plan. This intra-operative fusion may be performed with software overlays or images or contours or may be performed cognitively where the operator aligns the treatment or imaging device based on visual side-by-side assessment of concordance with the treatment plan.

In accordance with an embodiment, a typical focal HIFU workflow may initially begin with positioning of a probe. For instance, the probe is positioned to aim at a lesion. Next, zones are planned and a high resolution scan is performed. A fusion may be performed in which an ultrasound or MR image is contoured and registered, the contours can be sent to a treatment device. A lesion contour may be expanded with a margin, applied, and edited. In accordance with a aspect, as described above, an improved workflow may involve pre-planning zones on MR, using predictive fusion to facilitate placement of the probe at a start of the procedure, and treating one or more zones in sequence. The treatment device may be prepared for predictive fusion, if needed.

In an embodiment, pre-planning may involve adding a margin to a lesion contour on MR image data. The margin may be custom, physician-specific, and may be automatically added. The MR images may be resliced to match a placement of a treatment probe. A virtual grid may be placed, or virtual HIFU zones may be overlaid on the MR images. In one example, a phantom may be loaded with a HIFU field of view and transmit zones. The phantom may be fused to the resliced images. A first zone is positioned by, for example, rotating if needed. The zone is edited to, for example, intersect with a lesion contour and remove portions of the zone not part of the lesion. These steps may be repeated to position additional zones. The contours and ultrasound are exported for predictive fusion, which may involve centroid-centroid alignment and one plan per zone. A transmit per zone is transferred to MR to accumulate.

To prepare for predictive fusion, an optional process may be performed. The optional process include selecting zones and entering a feature volume (e.g. a volume of an anatomical features such as a prostate). After import, a high resolution scan is performed. For fusion, a centroid of an image set is fused to a centroid of an acquired dummy 3D ultrasound. The contours can then be transferred back to a treatment device.

For predictive fusion, a probe may be positioned, manually in some embodiments, until an ultrasound image matches a contour from the MR zone plan. All 3 planes of a 3D image may be checked and the probe is adjusted as needed. Translation adjustment tools may be used if needed and rotation adjustments may be made by exporting the data.

In an embodiment, to treat a zone, a high resolution scan may be performed (if not already done). A target contour for the zone is set, the lesion is applied and/or edited. Then, the zone is treated.

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such features may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. A system, comprising:
   a processor coupled to memory storing computer-executable instructions that, when executed by the processor, configure the processor to:
   apply a treatment template to an image of a first imaging modality, the treatment template indicates a field of view of a treatment device and a plurality of ablation zones of the treatment device within the field of view;
   determine a zone-specific target area for each of the plurality of ablation zones associated with the treatment device; and
   register the image along with at least one of the zone-specific target area or the feature information to a second imaging modality associated with the treatment device,
   wherein the treatment device is a high-intensity focused ultrasound device.

2. The system of claim 1, wherein the processor is further configured to obtain feature information indicative of one or more features in the image.

3. The system of claim 2, wherein the feature information specifies at least a target feature in the image, and wherein the zone-specific target area is a portion of a ablation zone of the plurality of ablation zones at least partially intersecting the target feature.

4. The system of claim 3, wherein the processor is further configured to apply a margin to the target feature prior to determining the zone-specific target area.

5. The system of claim 1, wherein the processor is further configured to reslice the image based on a predetermined orientation of the treatment device and update the feature information according to the resliced image.

6. The system of claim 1, wherein the processor is further configured to output predictive fusion information to the treatment device, the predictive fusion information being based at least in part on the image with the at least one of the zone-specific target areas or the feature information, which has been registered to the second imaging modality.

7. The system of claim 1, wherein the processor is further configured to combine the image with a phantom image that indicates the field of view and the plurality of ablation zones to generate the treatment template.

8. The system of claim 7, wherein the processor is further configured to resliced the image based on a predetermined orientation of the treatment device, wherein the resliced image is combined with the phantom image.

9. The system of claim 1, wherein the processor is further configured to generate the treatment template based on at least one of energy model or device information associated with the treatment device.

10. A method, comprising:
    obtaining image data in a first imaging modality, the image data being associated with feature information that indicates one or more features in the image data;
    applying a treatment template to the image data with feature information, the treatment template indicates a field of view of a treatment device and a plurality of ablation zones of the treatment device within the field of view, wherein the treatment device is a high-intensity focused ultrasound device;

generating a zone-specific target area for each of the plurality of ablation zones based on the feature information and the treatment template; and generating predictive fusion information for a second imaging modality associated with the treatment device based on one or more of the image data, the feature information, the treatment template, or the zone-specific target area.

11. The method of claim 10, wherein the feature information specifies at least a target feature in the image data, and wherein the zone-specific target area is a portion of a ablation zone of the plurality of ablation zones at least partially intersecting the target feature.

12. The method of claim 11, further comprising applying a margin to the target feature prior to determining the zone-specific target area.

13. The method of claim 10, further comprising reslicing the image data based on a predetermined orientation of the treatment device and updating the feature information according to the resliced image data.

14. The method of claim 10, wherein generating the predictive fusion information comprises registering the image data along with at least one of the zone-specific target area or the feature information to the second imaging modality associated with the treatment device.

15. The method of claim 10, further comprising generating the treatment template based on at least one of energy model or device information associated with the treatment device.

16. A non-transitory, computer-readable storage medium having stored thereon computer-executable instructions for a fusion engine, the instructions, when executed, configure a processor to:

obtain image data in a first imaging modality, the image data being associated with feature information that indicates one or more features in the image data;

apply a treatment template to the image data with feature information, the treatment template indicates a field of view of a treatment device and a plurality of ablation zones of the treatment device within the field of view, wherein the treatment device is a high-intensity focused ultrasound device;

generate a zone-specific target area for each of the plurality of ablation zones based on the feature information and the treatment template; and generate predictive fusion information for a second imaging modality associated with the treatment device based on one or more of the image data, the feature information, the treatment template, or the zone-specific target area.

17. The non-transitory, computer-readable storage medium of claim 16, further storing instruction that configure the processor to reslice the image data based on a predetermined orientation of the treatment device and updating the feature information according to the resliced image data.

18. The non-transitory, computer-readable storage medium of claim 16, further storing instruction that configure the processor to register the image data along with at least one of the zone-specific target area or the feature information to the second imaging modality associated with the treatment device to generate the predictive fusion information.

19. The non-transitory, computer-readable storage medium of claim 16, further storing instruction that configure the processor to generate the treatment template based on at least one of energy model or device information associated with the treatment device.

20. The non-transitory, computer-readable storage medium of claim 16, wherein the feature information specifies at least a target feature in the image data, wherein the zone-specific target area is a portion of a ablation zone of the plurality of ablation zones at least partially intersecting the target feature, and wherein the computer-readable storage medium further stores instructions that configure the processor to apply a margin to the target feature prior to determining the zone-specific target area.

* * * * *